US00PP14211P29

(12) United States Plant Patent
Yates

(10) Patent No.: US PP14,211 P2
(45) Date of Patent: Oct. 7, 2003

(54) ANTIRRHINUM PLANT NAMED 'YAHIT'

(50) Latin Name: *Antirrhinum*
Varietal Denomination: Yahit

(76) Inventor: Frederic Yates, Poplar Nursery Holmes Chapel Rd., Somerford, Congleton, Cheshire (GB), CW12 4FP ( * ) Notice: Subject to any disclaimer, the term of this patent is extended or adjusted under 35 U.S.C. 154(b) by 103 days.

(21) Appl. No.: 09/689,326

(22) Filed: Oct. 12, 2000

(51) Int. Cl.[7] ..... A01H 5/00
(52) U.S. Cl. ..... Plt./322
(58) Field of Search ..... Plt./322

(56) References Cited

U.S. PATENT DOCUMENTS

PP13,459 P2 * 1/2003 Yates ..... Plt./322

OTHER PUBLICATIONS http://www.inspection.gc.ca/english/plaveg/pbrpov/cropreport/snap/app00002725e.shtml.*
http://www.ecke.com/images/i_fields/photos/ff%20comb/happydayCB.pdf.*
http://www.plants–magazine.com/newplants/newplant7.shtml.*
van der Werff, Dirk. "New Cannas, and ten flowers per stem for Narcissus 'Golden Rules'". Plants Issue 13 1998.*

* cited by examiner

*Primary Examiner*—Bruce R. Campell
*Assistant Examiner*—W C Haas

(57) ABSTRACT

A new cultivar of Antirrhinum plant named 'Yahit' that is characterized by shorter internodes, compact and shapely habit, more flowers with an outward facing orientation and intense flower color containing more yellow than exhibited on any other trailing type of Antirrhinum.

2 Drawing Sheets

CROSS-REFERENCES TO RELATED APPLICATIONS

This application is related to U.S. Plant Pat. No. 13,459 and the previously filed applications entitled Antirrhinum Plants Named 'Yablu' (Ser. No. 09/520,231), 'Yapeep' (Ser. No. 09/520,230), 'Yaprim' (Ser. No. 09/520,227), 'Yarob' (Ser. No. 09/520,228), and 'Yalil' (Ser. No. 09/520,229), now abondoned.

BACKGROUND OF THE INVENTION

The present invention relates to a new and distinct cultivar of Snapdragon, known botanically as an Antirrhinum of hybrid origin and referred to hereinafter by the cultivar name 'Yahit'.

The new plant was selected by the inventor from his breeding program in a cultivated area of Congleton, Chesire, England. The objective of the program is to produce new cultivars of Snapdragons that have a trailing growth habit with a range of flower color and an outward presentation of the flowers. Seedlings were first crossed in the summer of 1998 by the inventor in Congleton, Chesire, England. The parents are unintroduced Antirrhinums of hybrid origin from the inventors breeding program. 'Yahit' originated from a seed bed containing open pollinated hybrids of *Antirrhinum gluutinosum×majus* (not patented) and *Antirrhinum braun-blanquettii* (not patented). The exact parents are unknown. The final seedling selection of 'Yahit' was made in May 1999 by the inventor.

'Yahit' is distinguished by shorter internodes, a more compact form, more shapely trailing habit, more abundant flowers with a stronger intense flower color and a greater amount of yellow than any other trailing type Antirrhinum. The closest comparative cultivars to 'Yahit', are 'Yacan'(not patented), 'Yaprim', 'Layel' U.S. Plant Pat. No. 9,985 and 'Yablu'. 'Yahit' differs from 'Yacan' in its shorter internodes, more shapely and compact habit, increased number of flowers and more intense yellow flower color. 'Yahit' differs from 'Yaprim' in its solid intense yellow flower color and absence of primrose-colored veining. 'Yahit' differs from 'Yablu' and 'Layel' in its uniform, intense yellow flower color and flowers that face consistently outward.

'Yahit' is distinguished by larger flowers than *Antitirrhinum gluutinosum×majus* that are a brighter yellow. 'Yahit' flowers are a brighter yellow than the flowers of *Antirrhinum braun-blanquettii.*

The first asexual propagation, using cuttings, was conducted in June 1999 by the inventor in Congleton, Chesire England. Three successions of cuttings were taken and varietal stability was insured. The characteristics of this cultivar have been determined stable and are reproduced true to type in successive generations.

SUMMARY OF THE INVENTION

The following traits have been repeatedly observed and represent the characteristics of the new cultivar. These attributes in combination distinguish the new cultivar from all other varieties. 'Yahit' exhibits a compact and shapely habit, exhibiting shorter internodes and an increased abundance of flowers with an outward presentation and a more intense yellow coloring than any other trailing type Antirrhinum known to the inventor.

BRIEF DESCRIPTION OF THE DRAWINGS

The accompanying color photographs illustrate the overall appearance of the new cultivar.

The first drawing illustrates the foliage, flower color and presentation, and habit.

The second drawing compares a flower of 'Yahit' on the right with a flower of 'Layel' on the left. All photographs are taken of 6 month old plants grown in one-gallon containers under greenhouse conditions in Encinitas Calif. The prints are made using conventional photographic techniques and although colors may appear different from actual colors due to light reflectance, they are as accurate as possible by conventional photography.

BOTANICAL DESCRIPTION OF THE PLANT

The following is a detailed description of a 6 month old plant of the new cultivar as grown in a one-gallon container under greenhouse conditions in Encinitas Calif. Phenotypic differences may be observed with variations in environmental, climatic, and cultural conditions. The color determinations are in accordance with The Royal Horticultural Society Colour Chart except where general color terms of ordinary dictionary significance are used. The growing requirements are similar to the species and no growing problems have been observed.

Botanical classification: *Antirrhinum glutinosum×majus* 'Yahit'.
Common name: Snapdragon.
Use: Hangirg basket or patio plant.
Parentage:
- *Seed parent.*—Unknown Antirrhinum hybrid.
- *Pollen parent.*—Unknown Antirrhinum hybrid.

Propagation: Tip cuttings.
Type: Vegetative annual.
Root system: Fibrous.
Time to initiate roots: 10 days at 20 degrees Celsius.
Height and spread: 30–35 cm high by 35–40 cm wide.
Branching arrangement: Freely branching.
Plant habit: Compact and cascading.
Hardiness: −10 Centigrade.
Stem shape: Cylindrical.
Stem color: 144B.
Stem size: 19 cm long by 3 mm wide.
Secondary stem size (or peduncles): 9 cm long by 2 mm wide.
Internode length: 1 to 1.5 cm between nodes.
Stem surface: Glabrous.
Foliage:
- *Leaf arrangement.*—Opposite.
- *Leaf division.*—Simple.
- *Shape.*—Ovate.
- *Base.*—Cuneate.
- *Apex.*—Acute.
- *Venation.*—One prominent mid-vein.
- *Surface.*—Glabrous.
- *Length.*—2 cm long.
- *Width.*—75 cm wide.
- *Leaf color* (*upper surface*).—139A.
- *Leaf color* (*lower surface*).—139B.
- *Petiole length and width.*—4 mm long by 1 mm wide.
- *Petiole color.*—138B.

Flower buds:
- *Bud dimensions.*—1.25 cm in length, 0.75 cm in width.
- *Bud color.*—157B.

Flower:
- *Type.*—Bilabiate in leafy terminal racemes, zygomorphic.
- *Arrangement.*—Opposite.
- *Margins.*—Entire.
- *Texture.*—Smooth.
- *Color of upper lip.*—10D.
- *Color of lower lip.*—10D.
- *Color of lower lip palate.*—9A.
- *Color of corolla tube.*—9A.
- *Fragrance.*—Slight perfume scent.
- *Flower height.*—3 cm high.
- *Flower length.*—2 cm long.
- *Flowering season.*—Spring, summer and fall.
- *Time to produce flowers.*—12 to 16 weeks.
- *Flowering time.*—Diurnal.
- *Lastingness.*—7 to 10 days.
- *Aspect.*—Flowers facing outward.
- *Peduncle length.*—6 mm long.
- *Peduncle width.*—2 mm wide.
- *Peduncle color.*—138B.
- *Persistent or non-persistent.*—Persistent.
- *Petals.*—Two petals.
- *Petal length.*—3.5 cm long.
- *Petal width.*—2.5 cm wide.
- *Fused or unfused.*—Petals fused.
- *Petal color* (*opening*).—145C.
- *Petal color* (*mature*).—Lower lip 3C, upper lip 2 A, outer tube 155A.
- *Calyx size.*—50 cm long and 20 cm wide.
- *Sepals.*—Five sepals.
- *Sepal color.*—138C,B.

Reproductive organs:
- *Stamens.*—4.
- *Stamen dimensions.*—2.5 cm in length, 1 mm in width.
- *Anther attachment.*—Dorasfixed.
- *Anther dimensions.*—2 mm in length, 1 mm in width.
- *Anther color.*—13A.
- *Pollen color.*—15A.
- *Pollen amount.*—Moderate.
- *Staminode.*—1.
- *Pistil.*—1.
- *Pistil dimensions.*—15 mm in length, 1 mm in width.
- *Pistil color.*—69A.
- *Style dimensions.*—3 mm in length, 1 mm in width.
- *Style color.*—145A.
- *Stigma dimensions.*—3 mm in length, 3 mm in width.
- *Stigma color.*—144B.
- *Ovary shape.*—Globose.
- *Ovary position.*—Superior.
- *Ovary dimensions.*—3 mm in length, 3 mm in width.
- *Ovary color.*—145A.

Seed:
- *Seed shape.*—Ovoid.
- *Seed dimensions.*—1.5 mm in length, 0.75 mm in width.
- *Seed color.*—Black.

I claim:

1. A new and distinct cultivar of Antirrhinum plant named 'Yahit' as described and illustrated.

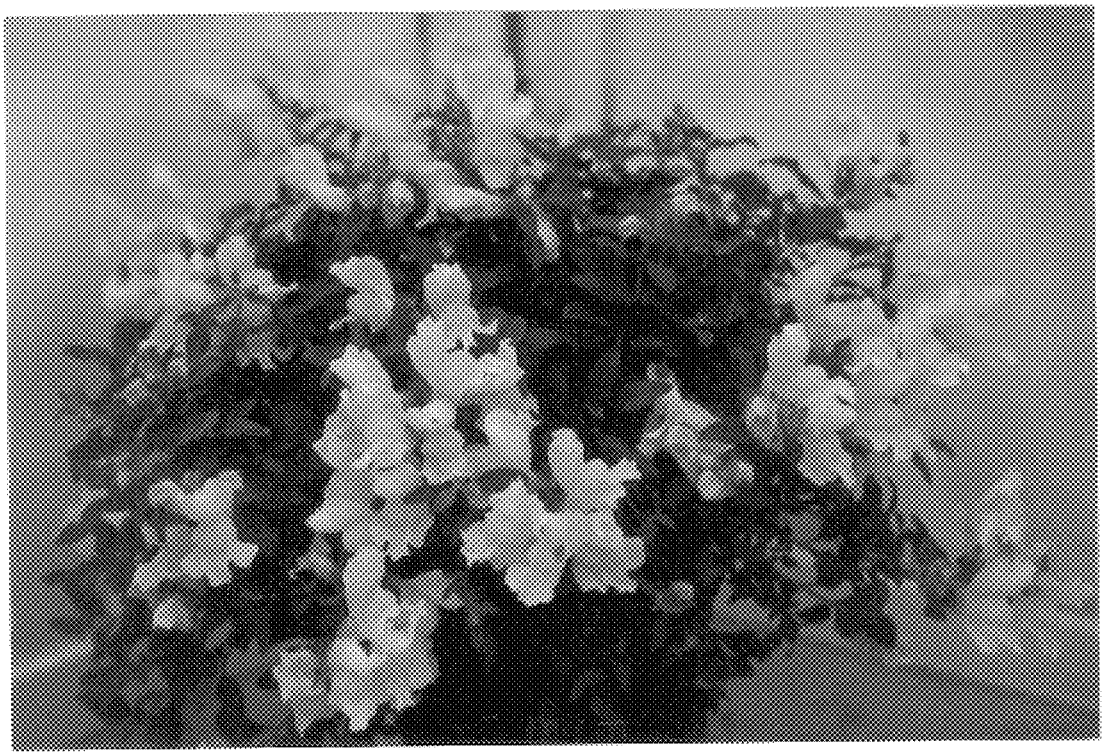

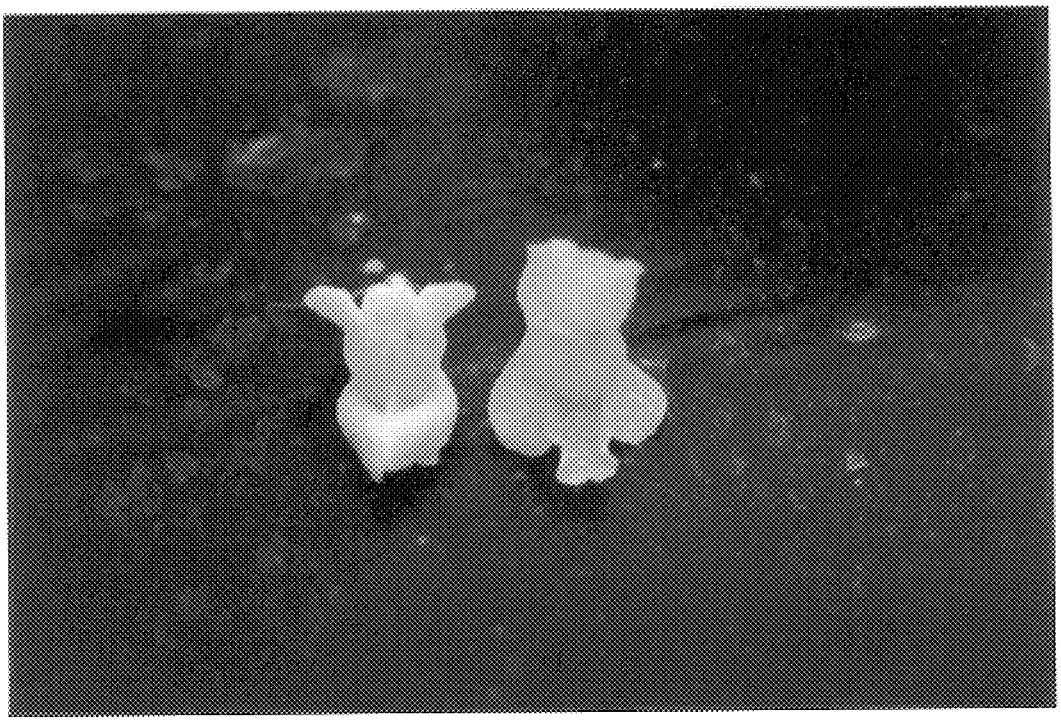

* * * * *